(12) United States Patent
Deshpande et al.

(10) Patent No.: US 7,439,385 B2
(45) Date of Patent: Oct. 21, 2008

(54) PROCESS FOR THE PREPARATION OF BIPHOSPHONIC DERIVATIVES

(75) Inventors: Pandurang Balwant Deshpande, Vadodara (IN); Parven Kumar Luthra, Vadodara (IN)

(73) Assignee: Alembic Limited, Gujarat (IN)

( * ) Notice: Subject to any disclaimer, the term of this patent is extended or adjusted under 35 U.S.C. 154(b) by 311 days.

(21) Appl. No.: 11/491,696

(22) Filed: Jul. 24, 2006

(65) Prior Publication Data

US 2006/0258625 A1 Nov. 16, 2006

(30) Foreign Application Priority Data

Feb. 20, 2006 (IN) .................. 240/MUM/2006

(51) Int. Cl.
*C07F 9/38* (2006.01)
*C07F 9/06* (2006.01)
(52) U.S. Cl. ............... 562/13; 546/22; 548/113; 548/119
(58) Field of Classification Search ............... 562/13; 546/22; 548/113, 119
See application file for complete search history.

(56) References Cited

U.S. PATENT DOCUMENTS

| 5,019,651 | A | * | 5/1991 | Kieczykowski | ............... 562/13 |
| 5,510,517 | A | * | 4/1996 | Dauer et al. | ................... 562/13 |
| 5,792,885 | A | * | 8/1998 | Ham et al. | ..................... 562/13 |

OTHER PUBLICATIONS

Kieczykowski et al., J. Org. Chem. 1995, 60, 8310-12.*

* cited by examiner

*Primary Examiner*—Kamal Saeed
*Assistant Examiner*—Robert Havlin
(74) *Attorney, Agent, or Firm*—Hamre, Schumann, Mueller & Larson, P.C.

(57) ABSTRACT

The present invention provides a novel process for preparation of bisphosphonic acid derivatives or pharmaceutical acceptable salt thereof, by reacting carboxylic acid having structural formula (II) with phosphorous acid and a halophosphorous compound, wherein halophosphorous compound is selected from the group comprising of $PCl_3$, $PCl_5$, $POCl_3$, $PBr_3$, $POBr_3$, and $PBr_5$ in presence of diphenyl ether.

3 Claims, No Drawings

PROCESS FOR THE PREPARATION OF BIPHOSPHONIC DERIVATIVES

FIELD OF INVENTION

The present invention relates to an improved process for the preparation of biphosphonic acids derivatives or pharmaceutical acceptable salts thereof.

BACKGROUND OF THE INVENTION

The biphosphonic acids derivatives are an important class of medicaments useful in the treatment of bone disorders such as Paget's disease and osteoporosis.

The bisphosphonic acids derivatives bisphosphonic acid derivatives or pharmaceutical acceptable salts thereof, having structural formula (I), Formula (I)

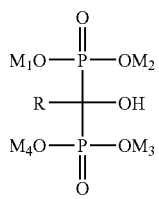

wherein $M_1, M_2, M_3, M_4$ represents H or a monovalent cation.
wherein R represents group as mentioned hereinbelow

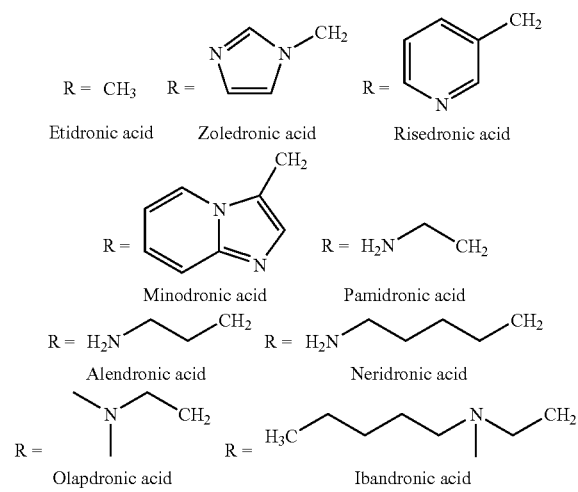

The synthesis of 1-hydroxy-1,1-biphosphonic acids are based on reacting a carboxylic acid with a mixture of phosphorous acid and phosphorous halides such as $PCl_3$, $PCl_5$, $POCl_3$, then quenching the reaction mixture with water or a nonoxidizing aqueous acid, followed by heating to hydrolyze the phosphorous intermediates to final product.

U.S. Pat. No. 4,621,077, which relates to the preparation of alendronic acid and neridronic acid, describes the preparation by treating carboxylic acid with a phosphonation reactant in the presence of chlorobenzene, followed by hydrolysis of the reaction mixture by the addition of concentrated hydrochloric acid and subsequent heating of said mixture. The said patent describes the use of three phosphonation mixtures: $H_3PO_3/PCl_3$, $H_3PO_3/PCl_5$ and $H_3PO_3/POCl_3$. The application of this technique leads to obtaining solid and unstirrable masses in the course of the reaction. It is little difficult to adapt these processes to an industrial scale up, since the reaction mixture of the phosphonation step is not homogenous and tends to solidify, preventing stirring, and also the yields obtained are not consistent. Under these conditions, the subsequent hydrolysis step entails substantial risk, due to the presence of small drops of $PCl_3$ occluded in the reaction mixture and which may cause local overheating on contact with the hydrolyzing agent and also explosion of the gases generated.

A series of other patents i.e. U.S. Pat. Nos. 4,407,761, 4,327,039, 4,304,734, 4,267,108, 4,054,598 envisages the use of chlorobenzene as reaction solvent, but also in these cases the drawback described above is again met with.

U.S. Pat. Nos. 4,922,007, 5,019,651 and 5,510,517, as well as J. Org. Chem. 60, 8310, (1995), envisage the use of methanesulphonic acid as reaction solvent. This makes it possible to obtain stirrable masses in the course of the reaction. However, this technique, as reported in J. Org. Chem. 60, 8310, (1995), involves risks of safety in that this solvent gives rise to uncontrollable reactions in the reaction conditions, when the temperature of the reacting mixtures exceeds 85° C.

WO9834940 employs polyalkylene glycols as reaction solvents for synthesizing alendronic acid; however, these solvents have a high cost and are difficult to eliminate from the finished product, given their high boiling point.

In WO0049026, starting from a nitrogen-protected derivative of β-aminopropionic acid to prevent the known problems of stirrability of the reaction mixture, use is made of orthophosphoric acid as the reaction means. The derivatization of the starting product in any case renders the method of synthesis unwieldy and involves the need for introducing additional steps for protection and deprotection.

U.S. Pat. No. 5,792,885 synthesizes pamidronic acid starting from a nitrogen-protected derivative of γ-aminobutyric acid, in aromatic hydrocarbons as the reaction solvents. This method presents the same drawbacks illustrated for the method described in WO0049026.

WO0110874 regards the use of methanesulphonic anhydride as the solvent for producing alendronic acid, but the high cost of the solvent makes the process commercially less attractive.

The complexity and high cost of the prior art procedures has created a need for an improved process for the preparation of bisphosphonic acid or salts. The present invention provides a solution to the problem presented by the prior art.

Surprisingly, present inventors have found that when the reaction is carried out in the presence of diphenyl ether, operationally simple and easily adaptable at an industrial scale.

SUMMARY OF THE INVENTION

A primary object of the present invention is to provide an improved process for the preparation of bisphosphonic acid derivatives or pharmaceutical acceptable salts thereof.

A further object of the present invention is to provide an improved process for preparing bisphosphonic acid derivatives, which is operationally simple, easy to handle and feasible at commercial scale.

Another object of the present invention is to provide cost effective process for the preparation of bisphosphonic acid derivatives or pharmaceutical acceptable salts thereof.

Yet another object of the present invention is to provide an improved process for the preparation of bisphosphonic acid derivatives or pharmaceutical acceptable salt thereof, comprising a step of, reacting carboxylic acid of formula (II),

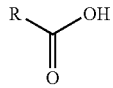

Formula II wherein R is same as define hereinabove, with phosphorous acid and halophosphorous compound, wherein halophosphorous compound is selected from the group comprising of $PCl_3$, $PCl_5$, $POCl_3$, $PBr_3$, $POBr_3$, and $PBr_5$ in the presence of diphenyl ether.

DETAILED DESCRIPTION OF THE INVENTION

Accordingly, the present invention relates to provide a process for preparing bisphosphonic acid derivatives or pharmaceutical acceptable salt thereof, having structural formula (I),

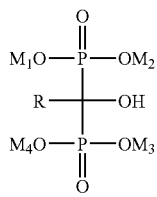

Formula (I)

wherein $M_1$, $M_2$, $M_3$, $M_4$ represents H or a monovalent cation.

wherein R represents group as mentioned hereinbelow

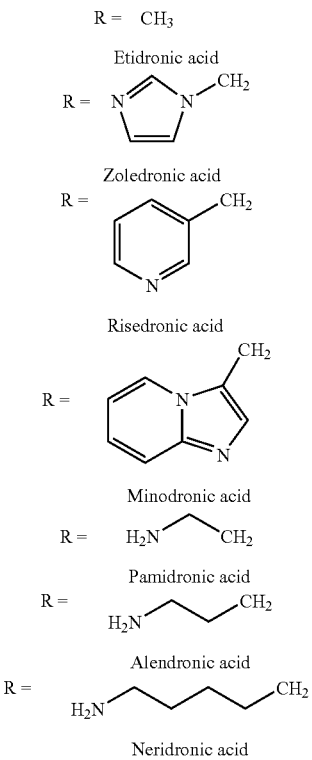

Olapdronic acid

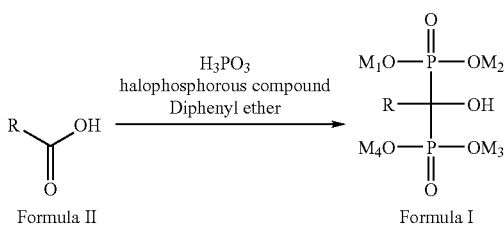

Ibandronic acid

The process of preparation of bisphosphonic acid derivatives or pharmaceutical acceptable salts thereof, comprising the step of reacting a carboxylic acid having structural formula (II) with phosphorous acid and a halophosphorous compound, wherein halophosphorous compound is selected from the group comprising of $PCl_3$, $PCl_5$, $POCl_3$, $PBr_3$, $POBr_3$, and $PBr_5$ in the presence of diphenyl ether.

The carboxylic acid of formula (II) wherein R is defined herein above. The suitable example of carboxylic acid included but not limited to 4-aminobutanoic acid, (3-pyridyl)ethanoic acid, (1-imidazoyl)ethanoic acid, N-(n-pentyl)-N-methyl-3-aminopropanoic acid, 2(imidazo[1,2-a]pyridin-3-yl)ethanoic acid, β-aminopropanic acid and 6-aminohexanoic acid. The selection of appropriate carboxylic acid depends on the end of bisphosphonic acid derivatives to be prepared.

The reaction is carried out at temperature ranging 50° C. to 100° C. Preferable temperature range is 65° C. to 75° C. The reaction is carried out generally for about 3 to 8 hours. After completion of the reaction water and toluene is added, heated and optionally the reaction mixture is charcoalized.

After filtering the aqueous layer and toluene layer is separated. Aqueous layer is concentrated and refluxed for 12 to 14 hours. The reaction mass is cooled at about RT and methanol is added and then cooled at about 0° C. The resultant isolated compound is dried at about 60° C.

The bisphosphonic acid derivatives of present invention can be converted into its salt using conventional method.

In a preferred embodiment, a process for the preparation of Alendronate sodium comprising a step of, a) reacting 4-amino butyric acid with phosphorous acid and a halophosphorous compound, wherein halophosphorous compound is selected from the group comprising of $PCl_3$, $PCl_5$, $POCl_3$, $PBr_3$, $POBr_3$, and $PBr_5$ in the presence of diphenyl ether to obtain Alendronic acid b) treating Alendronic acid with sodium hydroxide to obtain Alendronate Sodium The present invention process has advantages over prior art such as:

(i) It provides a process which is operationally simple and industrially applicable.

(ii) It involves less reaction time then prior art process.

(iii) It provides high yield.

The process of the present invention is described by the following examples, which are illustrative only and should not be construed so as to limit the scope of the invention in any manner.

EXAMPLES-1

Preparation of (4-Amino-1-hydroxybutylidene) Bisphosphonic Acid (Alendronic Acid)

The suspension of 4-amino butyric acid (10.0 g) and phosphorous acid (23.9 g) in diphenyl ether (50 ml) was heated up to 70° C. for 1 hour. Phosphorous trichloride (25.4 ml) was slowly added to reaction mass at 70° C. temperature and maintained reaction temperature for another 6 hours. Reaction mass was cooled to 25° C. followed by addition of water (150 ml) and toluene (30 ml). Reaction mixture was again heated to 70° C. and charged charcoal in hazy biphasic solution, stirred, filtered through Hyflo bed, washed the bed with hot water (30 ml). Layers was separated from filtrate, aqueous layer was washed with toluene (20 ml) and combined organic layer was then back extracted with water (20 ml) and mixed with main aqueous layer. The water (140 ml) was distilled out from combined aqueous layer at atmospheric pressure in 2 hours and then refluxed the concentrated mass for 13 hours. Reaction mass was cooled to 25° C. followed by addition of methanol (150 ml) in 1 hours. The reaction mixture was stirred and again cooled to 0° C. followed filtration. The filtrate was washed with chilled 1:2 mixture (30 ml) of water and methanol and dried at 60° C. to get Alendronic acid.

Yield: 19.0 gm (78.5%)

EXAMPLES-2

Preparation of Zoledronic Acid

The suspension of (1-imidazoyl)ethanoic acid (10.0 g) and phosphorous acid (19.5 g) in diphenyl ether (50 ml) was heated up to 70° C. for 1 hour. Phosphorous trichloride (20 ml) was slowly added to reaction mass at 70° C. temperature and maintained reaction temperature for another 6 hours. Reaction mass was cooled to 25° C. followed by addition of water (150 ml) and toluene (30 ml). Reaction mixture was again heated to 70° C. and charged charcoal in hazy biphasic solution, stirred, filtered through Hyflo bed, washed the bed with hot water (30 ml). Layers was separated from filtrate, aqueous layer was washed with toluene (20 ml) and combined organic layer was then back extracted with water (20 ml) and mixed with main aqueous layer. The water (140 ml) was distilled out from combined aqueous layer at atmospheric pressure in 2 hours and then refluxed the concentrated mass for 13 hours. Reaction mass was cooled to 25° C. followed by addition of methanol (50 ml) in 1 hours. The reaction mixture was stirred and again cooled to 0° C. followed filtration. The filtrate was washed with chilled 1:2 mixture (30 ml) of water and methanol and dried at 60° C. to get Zoledronic Acid.

Yield: 19.0 gm (75%)

EXAMPLES-3

Preparation of Risedronic Acid

The suspension of (3-pyridyl)ethanoic acid (10.0 g) and phosphorous acid (17.9 g) in diphenyl ether (50 ml) was heated up to 70° C. for 1 hour. Phosphorous trichloride (19.1 ml) was slowly added to reaction mass at 70° C. temperature and maintained reaction temperature for another 6 hours. Reaction mass was cooled to 25° C. followed by addition of water (150 ml) and toluene (30 ml). The reaction mixture was again heated to 70° C. and charged charcoal in hazy biphasic solution, stirred, filtered through Hyflo bed, washed the bed with hot water (30 ml). Layers was separated from filtrate, aqueous layer was washed with toluene (20 ml) and combined organic layer was then back extracted with water (20 ml) and mixed with main aqueous layer. The water (140 ml) was distilled out from combined aqueous layer at atmospheric pressure in 2 hours and then refluxed the concentrated mass for 13 hours. Reaction mass was cooled to 25° C. followed by addition of methanol (150 ml) in 1 hours, stirred and again cooled to 0° C., filtered, washed with chilled 1:2 mixture (30 ml) of water and methanol and dried at 60° C. to get Risedronic acid.

Yield: 19.0 gm (77%)

The invention claimed is:

1. A process for the preparation of bisphosphonic acid derivatives or pharmaceutical acceptable salt thereof, having structural formula (I),

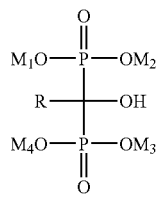

Formula (I)

wherein $M_1$, $M_2$, $M_3$, $M_4$ represents H or a monovalent cation, and R represents group as mentioned hereinbelow:

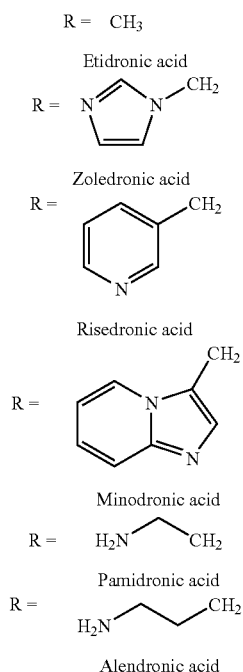

-continued

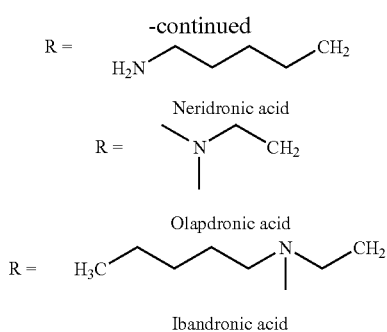

comprising a step of, reacting a carboxylic acid having structural formula (II)

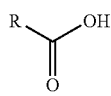

Formula II wherein R has the aforesaid meaning, with phosphorous acid and a halophosphorous compound, wherein halophosphorous compound is selected from the group comprising of $PCl_3$, $PCl_5$, $POCl_3$, $PBr_3$, $POBr_3$, and $PBr_5$ in the presence of diphenyl ether.

2. A process for the preparation of Alendronic acid comprising a step of, reacting 4-amino butyric acid with phosphorous acid and a halophosphorous compound, wherein halophosphorous compound is selected from the group comprising of $PCl_3$, $PCl_5$, $POCl_3$, $PBr_3$, $POBr_3$, and $PBr_5$ in the presence of diphenyl ether.

3. A process for the preparation of Alendronate sodium comprising steps of,
  a) reacting 4-amino butyric acid with phosphorous acid and a halophosphorous compound, wherein halophosphorous compound is selected from the group comprising of $PCl_3$, $PCl_5$, $POCl_3$, $PBr_3$, $POBr_3$, and $PBr_5$ in the presence of diphenyl ether to obtain Alendronic acid
  b) treating Alendronic acid obtained in step (a) with sodium hydroxide.

* * * * *